(12) United States Patent
Brekke

(10) Patent No.: US 7,524,514 B2
(45) Date of Patent: Apr. 28, 2009

(54) BIOMIMETIC COMPOSITION REINFORCED BY A POLYELECTROLYTIC COMPLEX OF HYALURONIC ACID AND CHITOSAN

(75) Inventor: John H. Brekke, Duluth, MN (US)

(73) Assignee: Tissue Engineering Consultants, Inc., Duluth, MN (US)

( * ) Notice: Subject to any disclaimer, the term of this patent is extended or adjusted under 35 U.S.C. 154(b) by 29 days.

(21) Appl. No.: 10/999,848

(22) Filed: Nov. 30, 2004

(65) Prior Publication Data

US 2005/0214341 A1    Sep. 29, 2005

Related U.S. Application Data

(60) Provisional application No. 60/525,965, filed on Dec. 1, 2003.

(51) Int. Cl.
| A61K 31/715 | (2006.01) |
| A61K 31/722 | (2006.01) |
| A61K 31/726 | (2006.01) |
| A61K 31/728 | (2006.01) |

(52) U.S. Cl. .................. 424/488; 424/484; 514/54; 514/55

(58) Field of Classification Search .................. None
See application file for complete search history.

(56) References Cited

U.S. PATENT DOCUMENTS

| 5,133,755 | A | 7/1992 | Brekke |
| 5,166,187 | A | 11/1992 | Collombel et al. |
| 5,306,311 | A * | 4/1994 | Stone et al. ............... 623/14.12 |
| 6,060,410 | A | 5/2000 | Gillberg-LaForce et al. |
| 6,482,231 | B1 | 11/2002 | Abatangelo et al. |
| 6,596,274 | B1 * | 7/2003 | Abatangelo et al. ........ 424/93.7 |
| 2002/0032488 | A1 | 3/2002 | Brekke et al. |
| 2004/0006146 | A1 | 1/2004 | Evans et al. |

FOREIGN PATENT DOCUMENTS

| EP | 0544259 A1 | 6/1993 |
| EP | 0640647 A2 | 3/1995 |
| EP | 0784985 A1 | 7/1997 |
| EP | 1003567 B1 | 5/2000 |
| WO | WO 02/30480 A1 | 4/2002 |
| WO | WO 03/008007 A2 | 1/2003 |

OTHER PUBLICATIONS

Takayama et al, Chem. Pharm. Bull, 1990, vol. 38, No. 7, pp. 1993-1997.*
Larsen, N.E. et al., *Effect of Hylan on Cartilage and Chondrocyte Cultures*, Journal of Orthopaedic Research, 10:23-32, 1992.
Morgelin, M. et al., *Assembly of cartilage proteoglycan with hyaluronate and structure of the central filament in proteoglycan aggregate*, Biochemical Society Transactions, 1990, p. 204-207.
Kvam, C. et al., *Purification and Characterization of Hyaluronan from Synovial Fluid*, Analytical Biochemistry, 211:44-49, 1993.
Hardingham, T.F. et al., *The specific interaction of hyaluronic acid with cartilage proteoglycans*, Biochim. Biophys. Acta, 279: 401-405, 1972.
Kekkonen, J. et al., *Adsorption Kinetics of Copmlexes Formed by Oppositely Charged Polyelectrolytes*, Journal of Colloid and Interface Science, 234: 384-392, 2001.
Luo, Y. et al., *Cross-linked hyaluronic acid hydrogel films: new biomaterials for drug delivery*, Journal of Controlled Release, 69: 169-184, 2000.
Luo, Y. et al., *Synthesis and Selective Cytotoxicity of a Hyalruonic Acid- Antitumor Bioconjugate*, Bioconjugate Chem 10: 755-763, 1999.
Blagosklonny, M.V. et al., *Molecular Effects of Paclitaxel: Myths and Reality (A Critical Review)*, Ing. J. Cancer 83:151-156, 1999.
Vercruysse, K.P. et al., *Synthesis and in Vitro Degradation of New Polyvalent Hydrazide Cross-Linked Hydrogels of Hyaluronic Acid*, Bioconjugate Chem. 8:686-694, 1997.
Balazs, E.A., *Medical Applications of Hyalruonan and its Derivatives*, Cosmetic and Pharmaceutical Application of Polymers, p. 293-310, 1991.
Knudson, C.B., *Hyaluronan Receptor-directed Assembly of Chondrocyte Pericellular Matrix*, The Journal of Cell Biology, vol. 120, No. 3, Feb. 1993, p. 825-834.
Neame, P.J. et al., *The link proteins*, Birkhauser Verlag Basel, 1993, p. 393-402.

(Continued)

Primary Examiner—L Blaine Lankford
Assistant Examiner—Allison M. Ford
(74) Attorney, Agent, or Firm—Pepper Hamilton LLP

(57) ABSTRACT

The present invention relates to a three dimensional, malleable cell culture composition and method of forming the same comprising hyaluronic acid, chitosan and a polyelectrolytic complex of hyaluronic acid and chitosan. These three components in combination constitute an initial microenvironment for support of stromal cells, and their undifferentiated mesenchymal cell progeny. The tissue engineering device and method of forming the same comprising hyaluronic acid and chitosan and the use of said device with compositions of pluripotent cells and various formulations of cell culture media for repair of tissues is disclosed.

16 Claims, 9 Drawing Sheets

(9 of 9 Drawing Sheet(s) Filed in Color)

OTHER PUBLICATIONS

Muzzarelli, R. et al., *Antimicrobial Properties of N-Carboxyburyl Chitosan*, Antimicrob. Agents and Chemotherapy, vol. 34, No. 10, Oct. 1990, p. 2019-2023.

Demarger-Andre, S. et al., *Chitosan carboxylic acid salts in solution and in the solid state*, Carbohydrate Polymers 23:211-219, 1994.

Kabanov, V.A. et al., *A New Class of Complex Water-Soluble Polyelectrolytes*, Makromol. Chem. Suppl. 6:259-276, 1984.

Takayama et al., *Effect of Interpolymer Complex Formation on Bioadhesive Property and Drug Release Phenomenon of Compressed Tablet Consisting of Chitosan and Sodium Hyaluronate*, Chem. Pharm. Bull. 38(7): 1993-1997, 1990.

Yan, X. et al., *PEC Films Prepared from Chitosan-Alginate Coacervates*, Chem. Parma. Bull 48(7): 941-946, 2000.

Hoffman, A.S., *Hydrogels for biomedical applications*, Advanced Drug Delivery Reviews 43: 3-12, 2002.

Tan, W. et al., *Evaluation of Nanostructured Composite Collagen-Chitosan Matrices for Tissue Engineering*, Tissue Engineering vol. 7, No. 2, p. 203-210, 2001.

Denuziere, A. et al., *Chitosan-chondroitin sulfate and chitosan-hyaluronate polyelectrolyte complexes. Physioco-chemical aspects*, Carbohydrate Polymers 29: 317-323, 1996.

Denuziere, A. et al., *Chitosan-chondroitin sulfate and chitosan-hyaluronate polyelectrolyte complexes: biological properties*, Biomaterials 19: 1275-1285, 1998.

Denuziere, A. et al., *Interactions between chitosan and glycosaminoglycans (chondroitin sulfate and hyaluronic acid): physicochemical and biological studies*, Ann Pharm Fr 58: 47-53, 2000.

Deb, A. et al., *Bone Marrow-Derived Cardiomyocytes are Present in Adult Human Heart: A Study of Gender-Mismatched Bone Marrow Transplantation Patients*, Circulation, Mar. 11, 2003, p. 1247-1250.

Prockop, D.J. et al., *One strategy for cell and gene therapy: Harnessing the power of adult stem cells to repair tissues*, PNAS, vol. 100, Suppl. 1, p. 11917-11923, Sep. 30, 2003.

Tateishi-Yuyama, E. et al., *Therapeutic angiogenesis for patients with limb ischaemia by automlogous transplantation of bone-marrow cells: a pilot study and a raadomised controlled trial*, The Lancet, vol. 360, p. 427-435, Aug. 10, 2002.

Sottile, V. et al., *Stem Cell Characteristics of Human Trabecular Bone-derived Cells*, Bone, vol. 30, No. 5, p. 699-704, May 2002.

Shih-Chieh, H. et al., *Isolation and Characterization of Size-Sieved Stem Cells from Human Bone Marrow*, Stem Cells 20: 249-258, 2002.

Bianco, P. et al., *Bone Marrow Stromal Stem Cells: Nature, Biology, and Potential Applications*, Stem Cells 19: 180-192, 2001.

Beresford, J.N., *Osteogenic Stem Cells and the Stromal System of Bone and Marrow*, Osteogenic Stem Cells 20: 270-280, Mar. 1989.

Ingber, D.E., *Tensegrity I. Cell Structure and Hierarchical Systems Biology*, Journal of Cell Science 116; 1157-1173, 2003.

Ingeber, D.E., *The Architecture of Life*, Scientific American, 48-57, Jan. 1998.

Lee et al., Preparation and Properties of Polyelectrolyte Complex Sponges Composed of Hyaluronic Acid and Chitosan and Their Biological Behaviors, J. Appl. Polymer Sci., Oct. 2003, vol. 90(4):925-932.

Yeh et al., Tissue Engineered Neocartilage Using Chitosan Gel and Chondrocytes, Dec. 1, 2002, Tissue Engineering 8(6):PP-72, Retrieved from the Internet on Mar. 27, 2008 at www.liebertonline.com/doi/abs/10.1089/107632702320934236.

Suh et al., Application of chitosan-based polysaccharide biomaterials in cartilage tissue engineering: a review, 2000, Biomaterials 21 (24):2589-2598.

Frenkel et al., Regeneration of articular cartilage-Evaluation of osteochondral defect repair in the rabbit using multiphasic implants. 2005, OsteoArthritis and Cartilage 13:798-807.

* cited by examiner

BIOMIMETIC COMPOSITION REINFORCED BY A POLYELECTROLYTIC COMPLEX OF HYALURONIC ACID AND CHITOSAN

FIELD

The present invention relates generally to malleable cell culture composition and methods of forming the same. The composition preferably comprises hyaluronic acid, chitosan and a polyelectrolytic complex comprised of hyaluronic acid and chitosan. It is believed that these components in combination constitute an initial microenvironment for support of stromal cells, and their undifferentiated mesenchymal cell progeny.

BACKGROUND

The field of tissue engineering relates to the technology of generating molecules, cells, tissues and, in rare instances, complete organs suitable for regenerating phenotypically specific tissue in host defects or injuries. Fundamental to the success of these efforts is understanding the mechanisms of cellular tensegrity by which undifferentiated pluripotent mesenchymal cells interpret information they receive from their microenvironments and translate these signals into biochemical messages capable of influencing expression of the genome.

Traditional in vitro cell culture methods employ two dimensional, polystyrene cell culture plates. While much valuable information has been discovered in such systems, two significant issues limit their application to tissue engineering problems. First, in vitro culture plates are generally rigid structures made, typically, of polystyrene. Secondly, in vitro culture plates provide the cells with only a two dimensional substratum. This two dimensional substratum is restrictive, since cells of tissues and organs respond to signals initiated within a three dimensional (3-D) microenvironment. Cells comprising all tissues, including bone, have some capacity to alter their three dimensional morphologies in response to changes in mechanical forces present within their environments.

Tissue engineering research has focused on the regeneration of bone and articular cartilage. Some remarkable successes toward these ends have been achieved by employing bioresorbable, synthetic compounds to fabricate anatomically and/or functionally specific, 3-D architectures by which biologically active agents and/or living cells are presented to bone or cartilage defects. One approach involves isolating cells from the body, expanding them in in vitro cultures, placing them on or within structural matrices, and implanting the new system inside the body. A commercial example of this approach is Carticell® (Genzyme Corp., Boston, Mass.), wherein a process and device that expands a patient's own articular cartilage cells (chondrocytes) in vitro and return them within a type I collagen matrix for treatment of articular cartilage defects. Another commercial construct known as Infuse® (Medtronic-Sofinore-Danek, Memphis, Tenn.) is a device composed of a type I collagen sponge saturated with a protein known as bone morphogenetic protein (recombinant human bone morphogenetic protein—2[rh-BMP-2]). This saturated sponge induces bone formation within the interbody spinal fusion model in the human.

Tissue engineering research has been directed toward: identification of appropriate cell sources (mature, pluripotent progenitor and stem cells); selection of suitable bioactive molecules (growth factors and morphogens); and fabricating devices of various compositions and geometries (synthetic or natural polymers, meshes or foams) to function as cell culture substrata. A three dimensional substratum may be described as an intricate biocompatible and bioresorbable network of natural or synthetic fibers defining an internal organization of spaces (voids) within which cells can grow, migrate, proliferate and differentiate if they are provided with a suitable extracellular matrix (ECM), and appropriately formulated nutrient media either in vitro or in vivo.

Adult bone marrow stromal cells, and their mesenchymal stem cell (MSC) progeny, have been shown to be pluripotent stem cells, capable of differentiating into cells of liver (hepatocyte), bone (osteoblast), fat (adipocyte), cartilage (chondrocyte), myocardium (cardiomyocyte), and the neuron.

Mesenchymal stem cells (MSC) are the formative pluripotential blast cells found inter alia in association with capillaries (i.e., the vascular pericyte) and bone marrow that are capable of differentiating into any of the specific types of connective tissue cells such as adipocytes, osteoblasts, chondrocytes, fibroblasts and myocytes (of smooth and skeletal muscle as well as the cardiomyocyte). Phenotype selection for the MSC is directed by various influences exerted by soluble bioactive factors such growth factors, morphogens and cytokines as well as information derived from their microenvironments by means of mechanochemical signal transduction. Although these cells are normally present at very low frequencies in bone marrow, through a process disclosed by Caplan and Haynesworth in U.S. Pat. No. 5,486,359 these cells may be isolated, purified and replicated in culture.

In order to isolate human mesenchymal stem cells (h-MSC), it is necessary to isolate rare pluripotent mesenchymal stem cells from other cells in the bone marrow or other MSC sources. Bone marrow cells may be obtained from the iliac crest, femur, tibia, spine, rib or other medullary spaces. Other sources of human mesenchyrnal stem cells include embryonic yolk sac, placenta, umbilical cord, fetal and adolescent skin, blood and other mesenchymal stem cell tissues.

Isolated human mesenchymal stem cell (h-MSC) compositions serve as progenitors for various mesenchymal cell lineages. Isolated mesenchymal stem cell populations have the ability to expand in culture without differentiating and have the ability to differentiate along specific connective tissue lineages when cultured in vitro or introduced in vivo at a place of damaged tissue. In order to realize the therapeutic potential of these cells to restore diseased or damaged connective tissues, they must be entrusted to a delivery vehicle possessed of biochemical and mechanical properties appropriate for propagation of a particular cell phenotype.

Several patents have attempted to describe a suitable biocompatible delivery vehicle for both undifferentiated and phenotypically mature cells. For example, U.S. Pat. No. 6,482,231 discloses a biological material for the repair of connective tissues comprising: a) a cell preparation enriched with mesenchymal stem cells, b) three-dimensional extracellular matrix comprising a hyaluronic acid derivative. This reference discloses the various ways to chemically treat hyaluronic acid to alter its biophysical and biological properties. For instance, U.S. Pat. No. 6,482,231 discloses treatment with formaldehyde or vinyl sulfone to give rise to crosslinked gels. In addition, various hyaluronic acid derivatives are disclosed, for example a partial or complete ester of hyaluronic acid with an aliphatic, aromatic or araliphatic alcohol, and a crosslinked hyaluronic acid derivative.

U.S. Pat. No. 6,596,274 discloses a biological material comprising two components, wherein the first component comprises alternatively (1) a culture of autologous or homologous bone marrow stem cells partially or completely differentiated into specific connective tissue cellular lines or (2) a sole extracellular matrix free from any cellular component secreted by the specific connective tissue cellular lines; and a second component comprises a three-dimensional biocompatible and biodegradable matrix consisting of a hyaluronic acid ester having a degree of esterification between 25 and 100%. The preferred hyaluronic acid ester disclosed is the benzyl alcohol ester having a degree of esterification varying from 25 to 100%.

U.S. Pat. No. 5,166,187 discloses a biomaterial consisting of an association of collagen, chitosan acetylated to a degree of acetylation between about 10% and about 40% and of glycosaminoglycans. The disclosed biomaterial is used for making extracellular matrices for regeneration of nerve cells and bones as well as biocompatible envelopes. A particular application is the making of artificial skin consisting of a dermal layer.

European Patent EP 1003567 B1 discloses a polysaccharide based gel which comprises: (1) chitosan or a chitosan derivative; and (2) a salt of polyol or sugar. The gel may be formed in situ within a tissue, organ or cavities of an animal or human.

European Patent Application EP 0784985 A1 discloses a bioabsorbable hydrophilic material comprising one or more compounds selected from a group consisting of gelatin, collagen, a collagen derivative, chitosan, a chitosan derivative, and triethanolamine alginate. A bone-forming graft is also disclosed comprising a bone morphogenetic protein and the bioabsorbable hydrophilic material.

European Patent Application EP 0544259 A1 discloses a water insoluble biocompatible hyaluronic acid polyion complex that comprises hyaluronic acid and at least one biocompatible high molecular compound having amino or imino groups. The polyionic complex is made by reacting an alkalimetal salt of hyaluronic acid with the high molecular compound in an organic acid aqueous solution.

PCT patent WO 03/008007 A2 discloses an implantable device for facilitating the healing of voids in bone, cartilage and soft tissue. The device includes a cartilage region comprising a polyelectrolytic complex joined with a subchondral bone region. Each of these regions comprise a macrostructure of a bioresorbable polymer. The device also includes a microstructure which is composed of various polysaccharides including hyaluronic acid. The polyelectrolytic complex transforms to hydrogel, following the implant procedure.

The present disclosure describes the use of a malleable cell culture matrix comprising both hyaluronan and chitosan as well as a polyelectrolytic complex (PEC) of the two constituents, that are combined in their dry states prior to the formation of the polyelectrolyte complex. The disclosure describes a new material that can function in vitro as an malleable cell culture material for pluripotent cells and subsequently perform as the delivery vehicle for implantation of these same cells into a host tissue. The present application refers to "hyaluronan" and "hyaluronic acid" as synonyms and both terms will therefore be used interchangeably.

SUMMARY

One embodiment of the present invention is a composition comprising: a hyaluronic acid viscoelastic gel, a chitosan hydrogel, and a network of polyelectrolytic complex fibers comprised of chitosan and hyaluronic acid. The compositions of the present invention may further comprise one or more biologically active agents, such as drugs, cytotoxic agents, pharmaceuticals, growth factor proteins, hormones, morphogens, phage vectors, viri vectors, artificial chromosomes, antibiotics, antineoplastics, and anticoagulants. In one embodiment, the biologically active agent is paclitaxel, which may be in the form of a bioconjugate of a low molecular weight hyaluronic acid and paclitaxel. The biologically active agent may include a protein selected from of the transforming growth factor-beta (TGF-$\beta$) family of proteins. The composition may further comprise pluripotent cells, such as stromal cells, mesenchymal stem cells, and mixtures thereof.

The chitosan hydrogel of the composition may be formed by adding an aqueous solution to dry protonated chitosan. The hyaluronic acid viscoelastic gel of the composition may be formed by adding an aqueous solution to dry hyaluronic acid. A malleable three-dimensional cell culture matrix and a tissue engineering material may be formed from the composition.

Also provided is a composition comprising: a reaction product of hydrated preprotonated chitosan and hydrated hyaluronic acid. Another embodiment is a composition formed by the process of: forming a mixture of dry hyaluronic acid and dry protonated chitosan, and adding an aqueous solution to the mixture. Another embodiment is a device for the delivery of tissue engineering materials comprising: a malleable cell composition comprising a hyaluronic acid viscoelastic gel, a chitosan hydrogel, and a network of polyelectrolytic complex fibers comprised of chitosan and hyaluronic acid, and a polymer.

The polymers of the device may be a rigid biodegradable homopolymer or a co-polymer comprising a biodegradable polymer, such as a poly-(alpha-hydroxy acid) polymer or caprolactone. The device may be a small diameter vascular graft. The polymer may be malleable non-biodegradable homopolymer or a co-polymer. The device may include biologically active agents and/or pluipotent cells.

Another embodiment is a method of forming a tissue engineering composition comprising: forming a mixture of dry hyaluronic acid and dry protonated chitosan, and adding an aqueous solution to the mixture, wherein the aqueous solution forms a network of polyelectrolytic complex fibers, and wherein the aqueous solution forms a hydrogel of homogeneous chitosan and a viscoelastic gel of homogeneous hyaluronic acid. In the method embodiments, the aqueous solution may be added dropwise. The mixture may be comprised of mechanically blended dry hyaluronic acid and dry protonated chitosan. The mixture may comprise about 0.25 to about 0.75 mole of hyaluronic acid to about 1 mole of chitosan and it may include an effective amount of hyaluronic acid to produce a predetermined amount of the network. The mixture may include an effective amount of chitosan to produce a predetermined amount of the network. The aqueous solution may be added in an amount of about 10:1 to about 15:1, based on the weight of the mixture. Method steps may include adding one or more biologically active agents and/or pluripotent cells.

Another embodiment is a method of delivering a composition into a host tissue, comprising: forming a mixture of dry protonated chitosan and dry hyaluronic acid, hydrating the mixture with an aqueous solution to form a network of polyelectrolytic complex fibers, adding a biologically active agent to the network, and delivering the network into a host tissue.

Another embodiment is a method of growing tissue in vivo comprising: injecting a tissue engineering material into mammalian host tissue, wherein the tissue engineering material comprises pluripotent cells, a hyaluronic acid component, a chitosan component, and a polyelectrolytic complex component comprised of chitosan and hyaluronic acid, and allowing the pluripotent cells to influence phenotypic choice of undifferentiated cells resident within the host tissue.

One embodiment provides a malleable cell culture device comprising unreacted regions of hyaluronic acid and chitosan invested with insoluble fibers of a polyelectrolytic complex composed of hyaluronic acid and chitosan. The device is capable of being metabolized by human stromal cells, mesenchymal cells and their more differentiated decendents. Another embodiment is a composition to serve as a medium for high concentration, regional delivery of biologically active agents.

BRIEF DESCRIPTION OF THE DRAWINGS

The file of this patent contains at least one photograph or drawing executed in color. Copies of this patent with color drawing(s) or photograph(s) will be provided by the Patent and Trademark Office upon request and payment of necessary fee.

The present invention will be better understood, when taken in conjunction with the following drawings, of which:

FIG. 10 represents viable cells after 5 days in culture, wherein a three dimensional, malleable cell culture composition has been used as a cell culture media according to one embodiment of the present invention.

DETAILED DESCRIPTION

Figure 1:
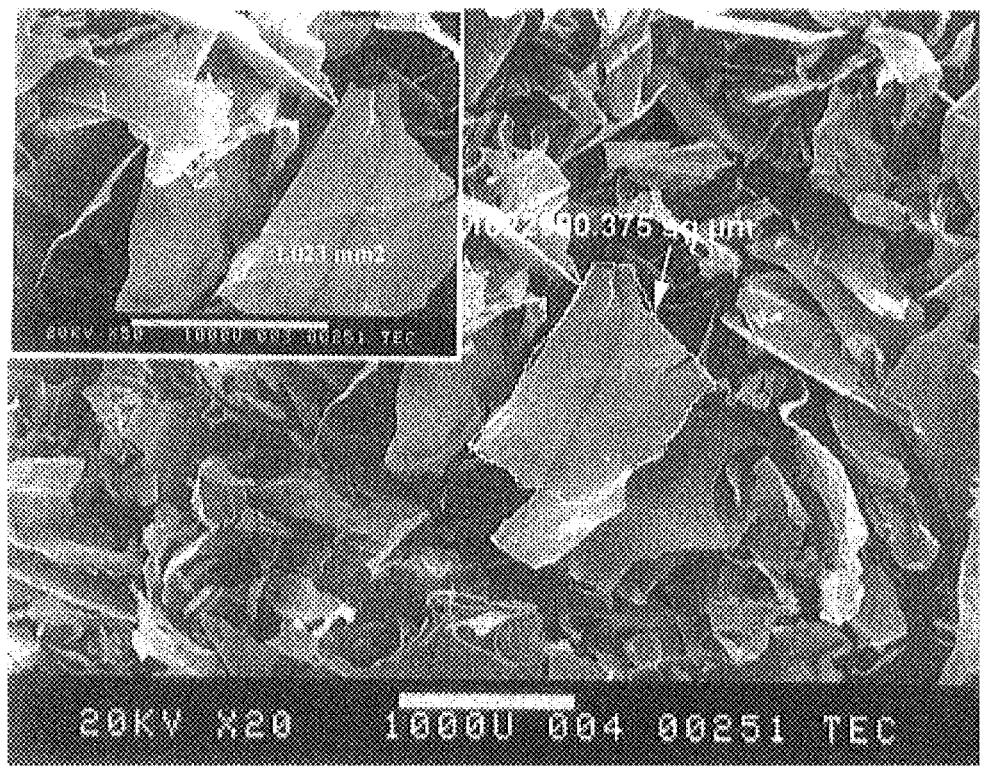
FIG. 1 represents a dry chitosan leaflet processed according to one embodiment of the present invention.

In the following description, numerous specific details are set forth in order to provide a thorough understanding of the invention. It will be apparent however, to one of ordinary skill in the art, that the invention may be practiced without limitation to these specific details. In other instances, well known methods and structures have not been described in detail so as not to unnecessarily obscure the invention.

It must be noted that as used herein and in the appended claims, the singular forms "a", "an", and "the" include plural reference unless the context clearly dictates otherwise. Thus, for example, reference to a "cell" is a reference to one or more cells and equivalents thereof known to those skilled in the art, and so forth. Unless defined otherwise, all technical and scientific terms used herein have the same meanings as commonly understood by one of ordinary skill in the art. Although any methods and materials similar or equivalent to those described herein can be used in the practice or testing of the present invention, the preferred methods, devices, and materials are now described. All publications mentioned herein are incorporated herein by reference, to the extent the reference provides support for the present application. Nothing herein is to be construed as an admission that the invention is not entitled to antedate such disclosure by virtue of prior invention.

Devices and methods are disclosed herein for treating mammalian bone, articular cartilage, cartilage of the nucleus pulposus and annulus fibrosus, myocardium and various other connective deficiencies, defects, voids and conformational discontinuities produced by congenital deformities, osseous and/or soft tissue pathology, traumatic injuries, and accidental, surgical, or functional atrophy. One device of the present invention provides an initial microenvironment within which human stromal cells, human mesenchymal cells and their differentiated progeny may be cultured in vitro and subsequently delivered into a host tissue defect and safely established therein within boundaries of invention. Thus, the present invention provides the means and environment for pluripotent cells to regenerate a specific tissue type, both in vitro and in vivo, for example, as the device is capable of being transplanted into connective tissue defects for the purpose of generating phenotypically specific repair tissue.

Aspects of the present invention relate to methods of forming a malleable hydrogel device with insoluble fibers or filaments therein, and of forming a three dimensional, random and irregular network of reinforcing fibers. The stiffness of the hydrogel component and density of reinforcing fibers are controlled in one method of the present invention to meet specific biologic demands of the cells to be grown within the device and to meet particular surgical handling requirements. The various compositions of the present invention are capable of being metabolized by human stromal and mesenchymal cells as well as other cells expressing the CD44 receptor.

One aspect of the present invention relates to a composition comprising a dry protonated chitosan and a dry hyaluronic acid. FIGS. 2-6 represent a mixture of dry hyaluronic acid and chitosan of one embodiment of the present invention. Another aspect of the present invention relates to a method of forming dry chitosan leaflets. FIG. 1 represents dry chitosan leaflets prepared by one method of the present invention.

Chitin is the major structural constituent of the exoskeleton of crustaceans and insects and is a component of the cell wall of fungi. Chitosan (poly-$\beta_{1-4}$-glucosamine) is the highly deacetylated form of chitin and is classified as an amino polysaccharide. Chitosan (CT) is protonated by exposure to either mineral or organic acid and is thus rendered soluble. Degree of CT protonation is related to solubility. A minimum of about 45% protonation of the available amine groups renders CT soluble. Preferably, chitosan is protonated from about 45% to about 100%. When exposed to pH levels below about 5.0, the amine groups (—$NH_2$) of chitosan molecules become protonated (—$NH_3^+$) thus rendering the molecules soluble in water and providing them with a strong positive charge (cation) that attracts negatively charged molecules (anions). Protonation of between about 45% and about 100% of available amine groups may be controlled to modify degree of interaction with the anion. At certain degrees of protonation, chitosan may be thought of as an amphoteric composition, meaning that it may both accept and donate protons, although chitosan is traditionally thought of as a cation in aqueous solution.

Protonation may occur by the exposure of chitosan to an acid to form a solution, preferably the substantially stoichiometric addition of an acid. The acid may be any inorganic or organic acid, preferably formic acid or glacial acetic acid. After the chitosan is protonated by exposure to an acid, the protonated CT solution may be lyophilized to a stiff porous chitosan fabric. The architecture of this CT fabric may be that of randomly sized, randomly shaped, intercommunicating interstices. CT fabric dimensions and physical properties may be controlled by the concentration of protonated CT in solution. The lyophilized CT fabric may be reduced to individual leaflets or platelets of dry protonated chitosan. These small pieces of CT fabric may have a thickness of about 1-10 micrometers and irregular planar shapes and dimensions. FIG. 1 represents a dry chitosan leaflet prepared according to one method of the present invention.

Chitosan may be obtained with a wide range of molecular weights up to weight average molecular weight of 1,000,000 or greater. In the preferred compositions of this invention, CT in the Mw range of 600,000 to 900,000 Da may be employed. However, it is recognized that greater or lesser Mw examples of CT may be employed to accommodate specific biologic requirements of cells to be cultured within its hydrogel or meet specific mechanical demands required of the final device.

Further, chitosan exhibits interesting biological properties that may be used clinically. It is hemostatic and cicatrizing and may be used as a cell culture support. Its antimicrobial capacity acts by stimulation of the immune system and, in particular, it induces the activation of macrophages.

Hyaluronic acid, also known as "hyaluronan," is a linear polyanionic polysaccharide, and is a member of the family known as glycosaminoglycans. It is present in most vertebrate connective tissues at relatively high concentrations (up to 10 mg/ml). Hyaluronic acid (HY) may be obtained with an original weight average molecular weight of about $1.8 \times 10^6$ Da. Upon size reduction to small particles, the Mw may be reduced to $1.0 \times 10^6$ Da. As with its chitosan partner in this construct, the molecular weight of HY may be altered to accommodate specific biologic demands of cells to be cultured. The basic structural unit of HY is a disaccharide consisting of D-glucuronic acid (GlcA) in $\beta_{1-3}$ linkage to N-acetyl-D-glucosamine (GlcNAc). The disaccharides may be linked together in a $\beta_{1-4}$ linkage. In its highly hydrated form, hyaluronic acid shows unique properties of viscoelasticity and plasticity.

In cartilage, hyaluronic acid plays a central role in the assembly and maintenance of the macromolecular components constituting the chondrocytes' extracellular matrix (ECM). It binds with high specificity and affinity to aggregan and link protein. A single hyaluronic acid chain may form a central "filament" that binds a large number of aggregan molecules, forming a supermolecular complex that immobilizes water and leads to a highly hydrated gel-like structure. In addition hyaluronic acid binds with high affinity to the chondrocyte CD44 receptor. Hyaluronic acid is naturally present in the vitreous humor of the eye and in the synovial fluid of joint cavities. It is used in surgical procedures involving the anterior chamber of the eye, such as corneal transplants and the removal and replacement of a cataractous lens. It is also used in the therapy of arthritis where injection of hyaluronic acid into the joint space may restore the rheological properties of the synovial fluid.

In its naturally occurring form hyaluronic acid is a salt, such as, for example, a sodium salt. The naturally occurring form may be subject to an ion exchange process to convert hyaluronic acid to an acid form. Although the acid form is preferred, both forms of hyaluronic acid may be used. Changing the naturally occurring form to an acid form may change the traditionally anionic hyaluronic acid to a more amphoteric substance, being able to both accept and donate protons in aqueous solution.

One embodiment of the present invention is a mixture of dry chitosan and dry hyaluronic acid, as shown in FIGS. 2-6. Preferably, the dry protonated chitosan is freeze-dried. The chitosan may be in the form of individual flakes or leaflets, as seen in FIG. 1. The individual flakes of chitosan comprise area dimensions of about up to 1 mm$^2$ and thickness dimensions of about 1-16 μm. The chitosan is preferably protonated to the degree of about 45% to about 100% of available amine groups.

Another aspect of the present invention relates to a composition comprising a hyaluronic acid viscoelastic gel, a chitosan hydrogel and a network of polyelectrolytic complex fibers surrounding and penetrating both the HY viscoelastic gel and the CT hydrogel. Another aspect of the present invention relates to a method of combining hyaluronic acid with chitosan in their dry states and adding an aqueous solution to this dry blend of reactants.

Figure 7:
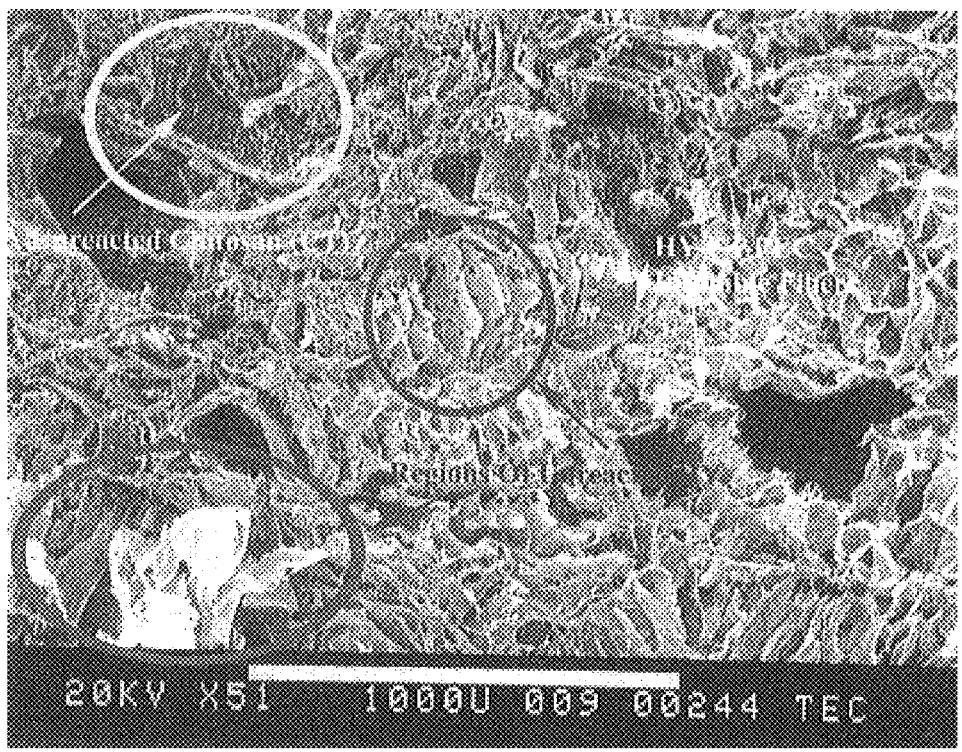
FIG. 7 shows the reaction product after the hydration of the dry hyaluronic acid and chitosan reactants according to one embodiment of the present invention.

The mixtures of dry HY and dry CT may be hydrated by an aqueous solution to form a reaction product. Once introduced to water, hyaluronic acid forms a viscoelastic gel, while chitosan forms a hydrogel. The two reactants form a polyelectrolytic complex at the regions of the intimate physical contact. FIG. 7 represents a post-reaction composition according to one embodiment of the invention. After reaction, there are regions of a homogeneous viscoelastic gel and a homogeneous hydrogel, remaining unreacted. Surrounding and penetrating these homogeneous regions of viscoelastic gel and hydrogel is a three-dimensional network of insoluble fibers comprising a polyelectrolytic complex of both CT and HY. See FIG. 7.

Polyelectrolytic complex (PEC) filaments may be formed from glycosaminoglycans (GAG's) serving as the anion reacted with polycations as well as other similarly structured compounds. While having the requisite electron affinity for bonding, some of the sulfonated GAG's may not be effective in supporting the appropriate cell-types. The PEC fibers may be made from hyaluronic acid (HY), a non-sulfonated GAG, and chitosan in one embodiment of the present invention.

While not wishing to be bound by theory, once introduced to an aqueous media, the strong negative charge associated with HY (anion) may be provided by the carboxylic acid group (—COO$^-$H$^+$) of its glucuronic acid moiety. The amine groups (—NH$_2$) of chitosan molecules have been protonated (—NH$_3^+$), thus rendering the molecules soluble in water and providing them with a strong positive charge (cation) that attracts negatively charged molecules, such as hyaluronic acid in solution, thus forming strong electrostatic interactions between the two reactants. However, since both the degree of protonation of the chitosan and the form of HY (acid or salt form) may be varied, both compounds may be amphoteric, having the ability to both accept and donate protons, in aqueous based solutions. Although HY is traditionally thought of as the anion and chitosan is traditionally thought of as the cation in aqueous solution, such strict labels may not be appropriate as pH, degree of protonation, and the form of HY (salt or acid based) may be varied and optimized.

In the prior art, when a solution of protonated chitosan is exposed to a solution of HY, a polyelectrolytic complex (PEC) is formed. In contrast, the reaction product of hydrated CT and HY, according to embodiments of the present invention, may be referred to as a PEC fiber reinforced hydrogel. Compounds resulting from these strong electrostatic interactions are also known as polyionic complexes (PIC). See FIG. 7.

Figure 5:
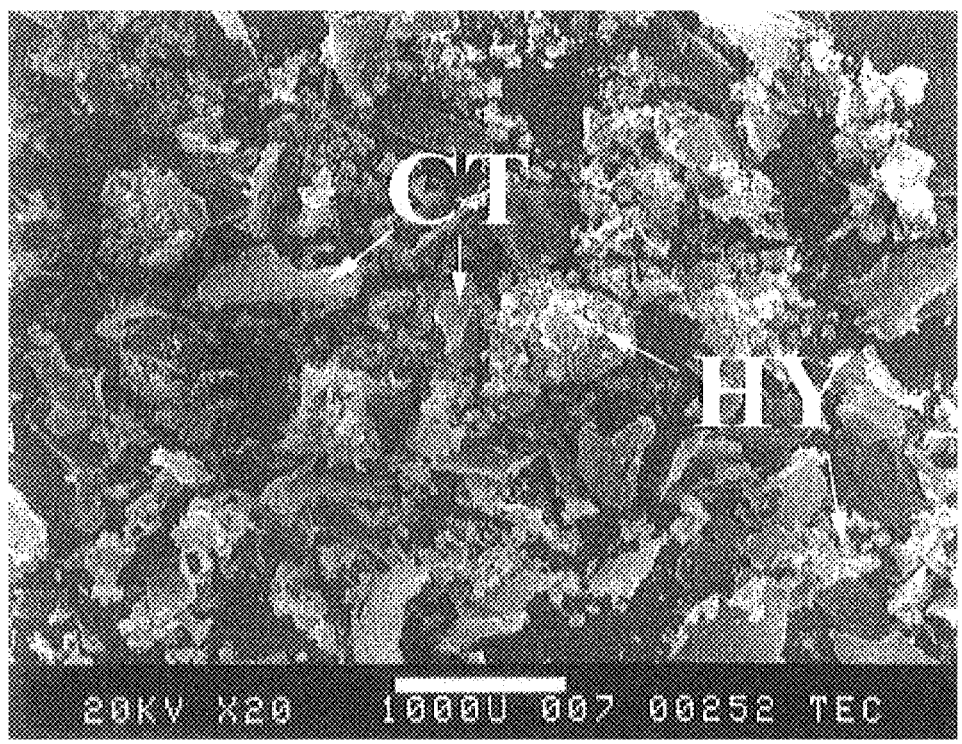
FIGS. 5 and 6 show, at low magnification, the two reactants, hyaluronic acid and chitosan, in their dry blended forms according to one embodiment of the present invention.

In one embodiment of the invention, proportions for the reactants and their physical sizes and locations relative to each other in the dry state may be precisely controlled so that the homogeneous regions of HY viscoelastic gel and CT hydrogel remain adjacent to one another while the insoluble fibers of the PEC surround and penetrate both regions. In their dry states, the leaflets of chitosan and the particles of hyaluronic acid are thus mechanically blended in appropriate mass ratios. FIG. 5 represents the blended dry reactants, according to one embodiment of the present invention.

For example, the dry CT and HY reactants may be mechanically blended in the range of about 0.25 to about 0.75 moles of HY for every about 0.6 to about 1.0 moles of CT. The dry reactants may be blended together in a high speed blender, for example. The lyophilized CT may optionally be reduced to leaflets separately in the blender, prior to the addition of dry HY to the blender. The blender may have blades that rotate at speeds in excess of about 30,000 rpm.

In another embodiment, the dry anion and cation reactants are hydrated with sterile water, sterile saline or other solution suitable for human injection. These solutions may contain biologically active agents such as drugs, cytotoxic agents, pharmaceuticals, growth factor proteins, hormones, morphogens, phage vectors, viri vectors, artificial chromosomes, antibiotics, antineoplastics, and anticoagulants. For example, the water or saline may contain the pharmaceutical, paclitaxel, conjugated with a low molecular weight hyaluronan. Though the resulting PEC fiber reinforced hydrogel is devoid of cells, it may be implanted in a host tissue void and function as a depot of biologically active agents at superphysiologic concentrations capable of attracting host cells into the construct and its vicinity and influencing their phenotypic choice upon their entry into the device.

In another embodiment, the mixture of dry HY and CT particulates may be exposed to nutrient media containing cells. The compositions and devices of the present invention therefore may comprise pluirpotent cells. The cell culture media may contain bone marrow stromal cells and mesenchymal cells as well as influential growth factors, morphogens and other biologically active agents. Upon exposure to the fluid of the culture media, the mixture of dry HY and CT particles may enter solution forming the PEC filaments while maintaining homogeneous regions of viscoelastic HY gel, and CT hydrogel. Where these reactants are proximate to one another, they react with each other to form the network of reinforcing PEC fibers. Attendant cells may be trapped within boundaries of the PEC fiber reinforced hydrogel. The entire hyaluronic acid-chitosan-polyelectrolytic complex hydrogel (HCP-h) may be described as a fluid mass, bounded by a defined network of thin membranes composed of PEC fibers.

This complex of HCP-h microenvironment may be invested with cells and their associated cell transfer solution and subsequently deposited into a sterile cell culture supplied with an excess of cell culture media. In this context the invention may function as a malleable, three dimensional, in vitro, cell culture matrix. Subsequently, it may be lifted en mass from its culture media and implanted into a host tissue as an in vivo tissue engineering device. The HCP-h microenvironment may also be a depot for high concentration regional delivery of drugs, growth factors, morphogens and other biologically active agents.

The water, water solution containing biologically active components, saline solution, cell culture media or cell transfer solution are referred to hereinafter as "water" for simplicity of discussing the hydration step of one embodiment of the present invention. The water may be added to a small sample of the dry blended HY and CT components, for example, in a drop-by-drop manner using a syringe. For example, about 10 µL to about 15 µL of water may be added for each 1 mg of dry reactants. This drop-by-drop placement of water on the dry component mixture may thus be controlled to create predetermined physical properties of the final reaction product.

Figure 8:
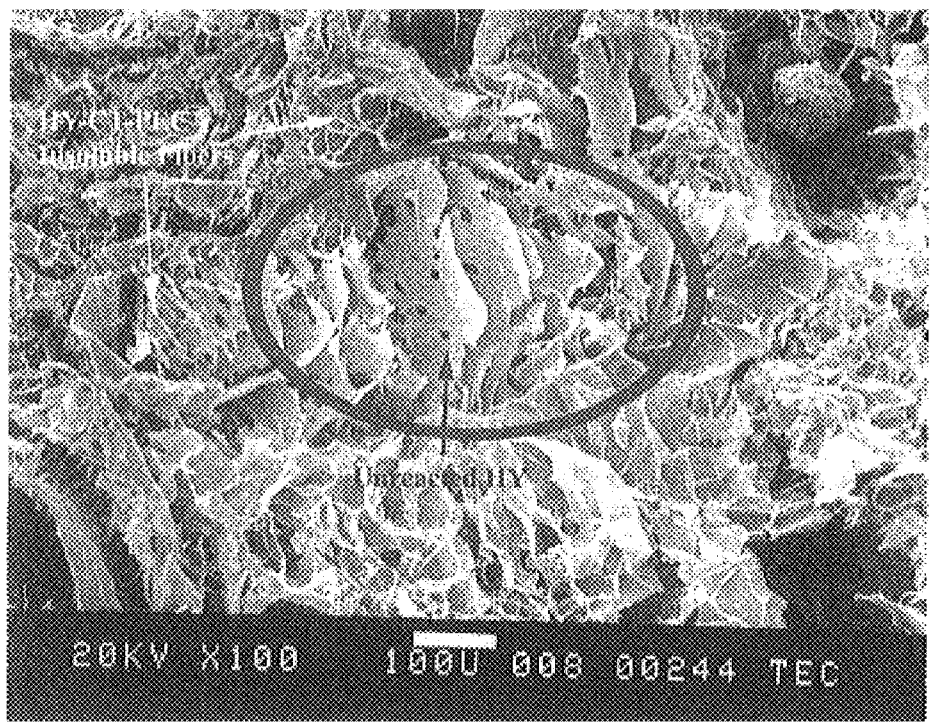
FIG. 8 shows a region of unreacted hyaluronic acid after lyophilization according to one embodiment of the present invention.
Figure 9:
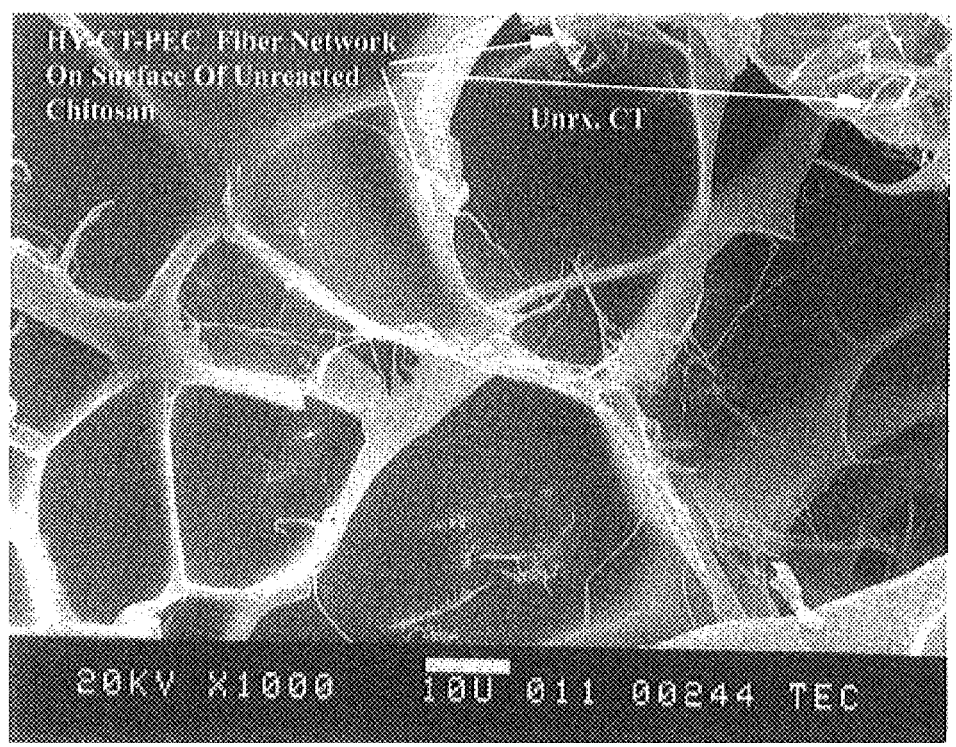
FIG. 9 shows the HY-CT-PEC fiber network on the surface of an unreacted chitosan leaflet after lyophilization according to one embodiment of the present invention.

One embodiment of the present invention relates to compositions comprising hyaluronic acid, chitosan, and the PEC fiber reinforced hydrogel formed by these two components. These compositions can be used as an extracellular matrix, a three-dimensional malleable cell culture complex, an injectable tissue engineering material or a depot for regional high concentration delivery of pluripotent cells, cytotoxic agents and other biologically active agents. The physical shape, size and mass ratio of the two reactant particles (in their dry states), as well as their positions of proximity to one another, may be used to govern chemical and physical properties of the resultant PEC fiber reinforced hydrogel. Upon hydration with sterile water, saline, cell culture media or cell transfer solution, the resulting complex contains multiple homogeneous regions of unreacted hyaluronic acid and unreacted chitosan surrounded by and penetrated by fibers of the polyelectrolytic complex. FIGS. 8 and 9 are representations of the HY-CT-polyelectrolytic complex, after lyophilization.

Another aspect of the present invention relates to a three dimensional device for the delivery of tissue engineering materials. Another aspect of the present invention relates to a method of forming a composition for the delivery of tissue engineering materials. Another aspect of the present invention relates to a method of implanting a composition into a host tissue in order to influence phenotypic choice of undifferentiated host (mesenchymal) cells. Another aspect of the present invention relates to a method of repairing tissue. A further aspect of the invention relates to a method of delivering cytotoxic agents and other pharmaceuticals to a particular anatomic site at high concentration.

Mesenchymal stem cells (MSC) are the formative pluripotential blast cells found inter alia in association with capillaries (i.e., the vascular pericyte), bone marrow, skeletal and smooth muscle, myocardium and other connective tissues that are capable of differentiating into any of the specific types of connective tissue cells such as adipocytes, osteoblasts, chondrocytes, fibroblasts and myocytes (of smooth and skeletal muscle as well as the myocardiocyte). In order to isolate human MSC, it is necessary to isolate rare pluripotent mesenchymal stem cells from other cells in the bone marrow or other MSC source. Bone marrow cells may be obtained from the iliac crest, femur, tibia, spine, rib or other medullary spaces. Other sources of human mesenchymal stem cells may include embryonic yolk sac, placenta, umbilical cord, fetal and adolescent skin, blood and other mesenchymal stem cell tissues.

Isolated human mesenchymal stem cell compositions serve as the progenitors for various mesenchymal cell lineages. Isolated mesenchymal stem cell populations have the ability to expand their numbers in culture without differentiating and have the ability to differentiate into specific phenotypic lineages when either induced in vitro or implanted in vivo at the place of the damaged tissue.

A sample of bone marrow may be obtained from a patient by aspiration from any one of several bone marrow deposits such as between cortical plates of the ileum. Once harvested, adherent cells of marrow specimen, consisting of bone marrow stromal cells (BMSC) and mesenchymal stem cells (MSC), are separated from the non-adherent cell fraction consisting of hematopoietic progenitor cells. The adherent cell moiety is culture expanded to tens of millions of cells per milliliter. Following culture expansion of adherent cell populations in two-dimensional culture environments and release from their points of attachment, aliquots of the cell/media suspension are withdrawn by a sterile, microliter pipette, centrifuged into a concentrated cell pellet, resuspended into a predetermined volume of cell transfer fluid (i.e., sterile saline or other balanced salt solution) and deposited upon a specific mass of the HCP-h material.

Prior to their introduction to the HCP-h material, it is recognized that the h-BMSCs and h-MSCs can be exposed to various growth factors and morphogens via the culture media, or transfected with various phage or viri vectors (i.e. retrovirus, adenovirus or artificial chromosome), in order to influence the phenotype selected by a preponderance of cells in the population. Also, growth factors, morphogens and other biologically active agents can be introduced into the cells' media prior to their placement into the HCP-h material to further influence their phenotypic choice and upregulate their endogenous production of the same growths factors or morphogens. Similarly, after the cell complex is created, comprising the HCP-h composition, it may be placed into an excess of cell culture media that contains particular morphogens and other biologically active agents that may diffuse into the cell complex and influence phenotypic selection of cells contained therein.

Another aspect of the present invention relates to a composition comprising a dry protonated chitosan, a dry high molecular weight moiety of hyaluronic acid and a dry bioconjugate of very low molecular weight hyaluronic acid and paclitaxel. Paclitaxel is a member of a class of drugs known as taxanes, which have been commercialized as a cancer medication under the trade name Taxol™. Paclitaxel has been known to slow or stop the growth of cancer cells in vivo and is normally insoluble in water. However, by conjugating paclitaxel with very low molecular weight examples of hyaluronan (for example, HY oligossaccharides of Mw 5,000 to low Mw examples of hyaluronic acid up to 60,000) it becomes soluble in water. Addition of lyophilized (dry) HY-paclitaxel bioconjugate to the various compositions of the present invention, such as the dry CT and dry HY composition, and further hydration produces a malleable depot of cytotoxic agent that may be implanted into a tissue defect created by excision of a malignant tumor or injected into a malignant tumor mass. For example the three components of dry CT, dry HY and the dry HY-paclitaxel bioconjugate could be hydrated according to a method of the present invention.

In an alternative embodiment, the dry HY particles and dry chitosan particles of one embodiment of the present invention may be hydrated with a solution of the HY-Paclitaxel conjugate, having a viscosity about equal to the viscosity of water, to form an HCP-h gel saturated with a predetermined concentration of HY-paclitaxel conjugate. The addition of the bioconjugate in solution results in the uniform distribution of the drug throughout the HCP-h gel.

In either embodiment of the hyaluronan-paclitaxel, hyaluronic acid, and chitosan reactions, there will be regions of unreacted HY, CT and HY-paclitaxel in addition to the reaction product, PEC, in the resulting post-reaction composition. The conjugate does not interact as an anion with chitosan (cation) in the reaction. The conjugation of paclitaxel to hyaluronan requires an attachment of intermediaries to hyaluronan's carboxylic acid group ($-COO^-H^+$), thus eliminating availability of the hyaluronan component of the conjugate as an anionic partner to CT in the subsequent reaction. Thus, post-reaction, the HY-paciltaxel bioconjugate remains a homogeneous, unreacted entity informally throughout the HCP-h volume.

Another embodiment of the present invention is a three dimensional device for the delivery of tissue engineering materials comprising the HCP-h material, and a rigid biodegradable homopolymer or co-polymers of rigid biodegradable polymers. Suitable homopolymers include those of the poly(alpha-hydroxy acid) group or poly-$\epsilon$-caprolactone. Suitable co-polymers of rigid biodegradable polymers include, for example, D,D-L,L polylactic acid-co-glycolide.

Another embodiment of the present invention is a three dimensional device for the delivery of tissue engineering materials comprising the HCP-h material, and a malleable non-biodegradable homopolymer or co-polymers of malleable non-biodegradable polymers. Suitable malleable non-biodegradable polymers include, for example, various species of polyurethanes.

The compositions according to the various embodiments of the present invention may also contain additional components, such as morphogens that are able to direct and enhance differentiation of mesenchymal stem cells along a desired phenotypic lineage. Such bioactive factors or combinations of factors are effective to induce differentiation of MSCs in host tissue according to the present invention into a phenotypic lineage selected from the group consisting of osteogenic, chondrogenic, tendonogenic, ligamentogenic, myogenic, marrow stromagenic, adipogenic, and dermatogenic.

In specific examples, the bioactive factor is a protein belonging to the transforming growth factor-$\beta$ super family (TGF-$\beta$), such as TGF-$\beta_1$, TGF-$\beta_3$, or bone morphogenetic protein (BMP) proteins. Other useful bioactive factors that could be delivered by the present invention include, but are not limited to, platelet derived growth factor (PDGF), insulin-like growth factor (IGF), and fibroblast growth factor (FGF) and its several analogues.

Other therapies, including but not limited to drugs, biologically active agents, and other agents, may also be utilized in or with the HCP-h compositions; either to aid the function of the HCP-h or to cause other stimuli. The drugs, biologics, or other agents may be naturally derived or otherwise created (e.g. synthesized). For example, growth factors can be derived from a living being (e.g. autologous, bovine derived, etc.), produced synthetically, or made using recombinant techniques (e.g., rh-BMP-2). Regardless of the time of investment or incorporation of these materials, they may be in the form of solid particulates, solution, gel or other deliverable form. Utilizing gel carriers may allow for the materials to be contained after wetting, for some tailorable length of time.

Malleable non-biodegradable polymers, including polyurethanes (PU) or other materials used for development of small diameter vascular grafts may also be used in an embodiment of the present invention. The HCP-h substance may serve as a microstructure for these grafts, invested within the interstices of polyurethane tubes possessed of 3-D architectures within their walls. The architectures of the polyurethane grafts may be a network of randomly sized, randomly shaped, infinitely intercommunicating void spaces.

Polyurethane offers no physical resistance to the forces directing microstructure solutions toward interior spaces of its 3-D architecture. It is possible to saturate these interior void spaces with a blend of hyaluronic acid and pre-protonated chitosan rendered as dry powders of very fine particle size. The HY and CT powders may be added separately, sequentially, or in a dry mixture blend. The grafting manufacturing conditions preferable are sterile: For example, the following manufacturing parameters might be used to invest the void spaces of a polyurethane graft with the various HCP-h compositions of the present invention: a class 100 clean room, laminar air flow, very low humidity levels, very cool temps (i.e. 60-65° F.). Packaging the resulting HCP-h invested polyurethane graft preferably includes: air tight glass ampoules or blisters, inert package atmosphere ($N_2$/ argon). The HCP-h compositions of various embodiments of the present invention therefore may be invested as a microstructure within a malleable (polyurethane) macrostructure tube.

A small diameter vascular graft is an example of the HPC-h material and malleable polymer embodiment of the present invention. The preferred embodiment for this device would a manufactured substitute for the saphenous vein graft employed in coronary artery by-pass procedures. Additional applications of the vein graft with the HPC-h material may act as a microstructure are repair/regeneration of damaged urethra and peripheral nerve regeneration.

DETAILED DESCRIPTION OF THE DRAWINGS

Figure 2:
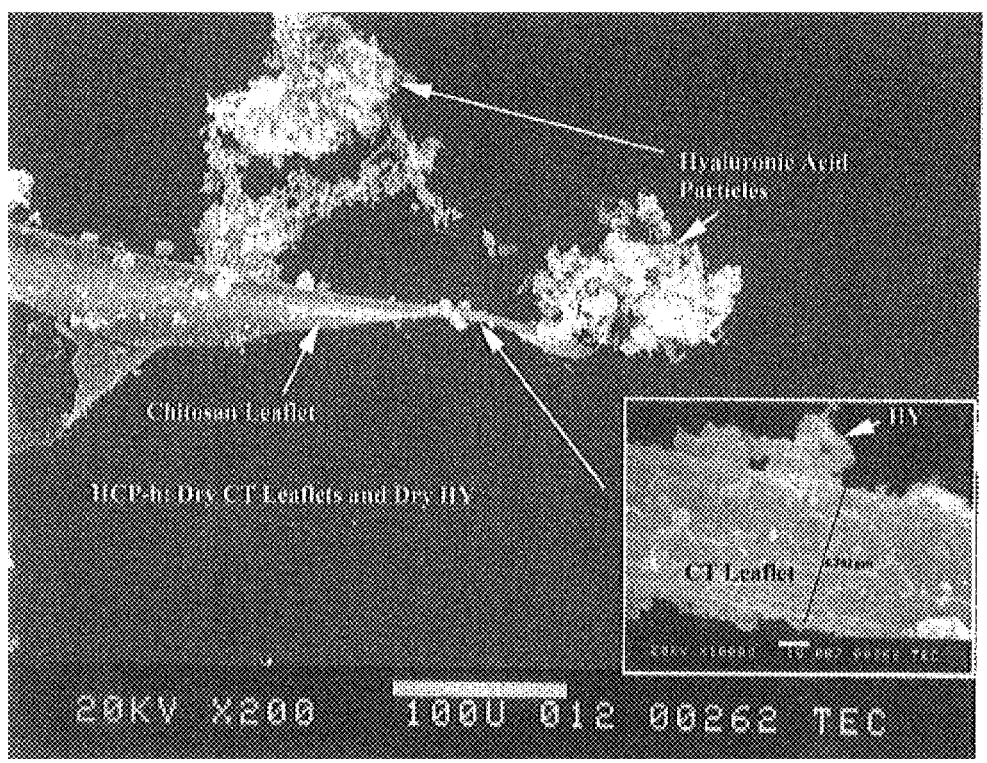
FIG. 2 represents a dry blend mixture of hyaluronic acid and chitosan according to one embodiment of the present invention.
Figure 3:
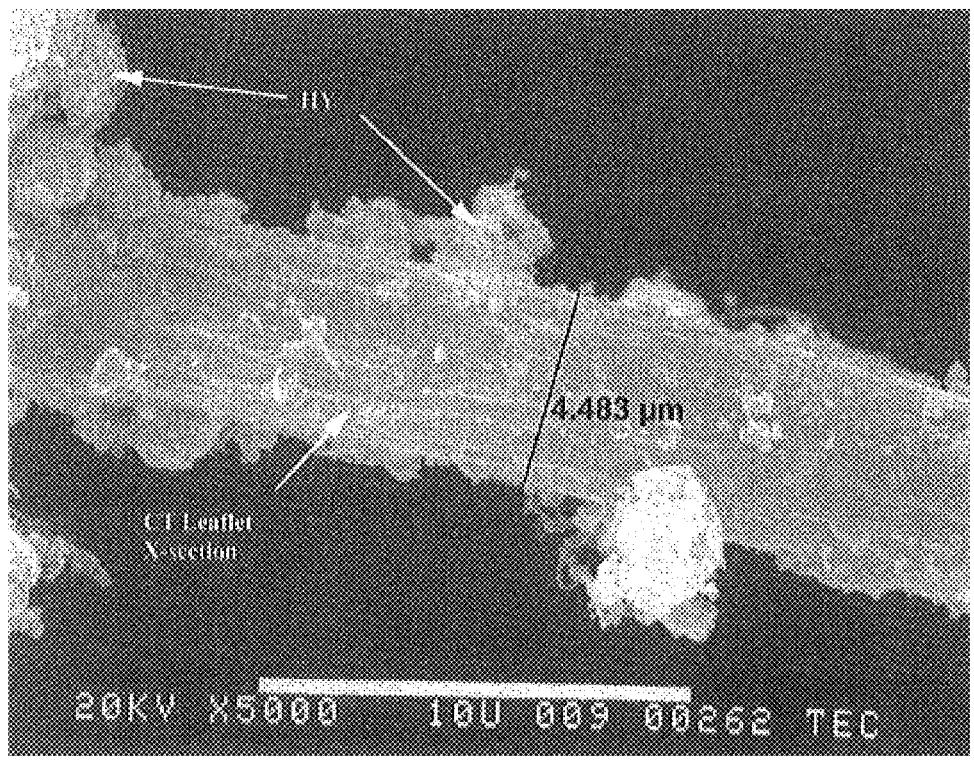
FIG. 3 represents a dry blend mixture of hyaluronic acid and chitosan according to one embodiment of the present invention.
Figure 4:
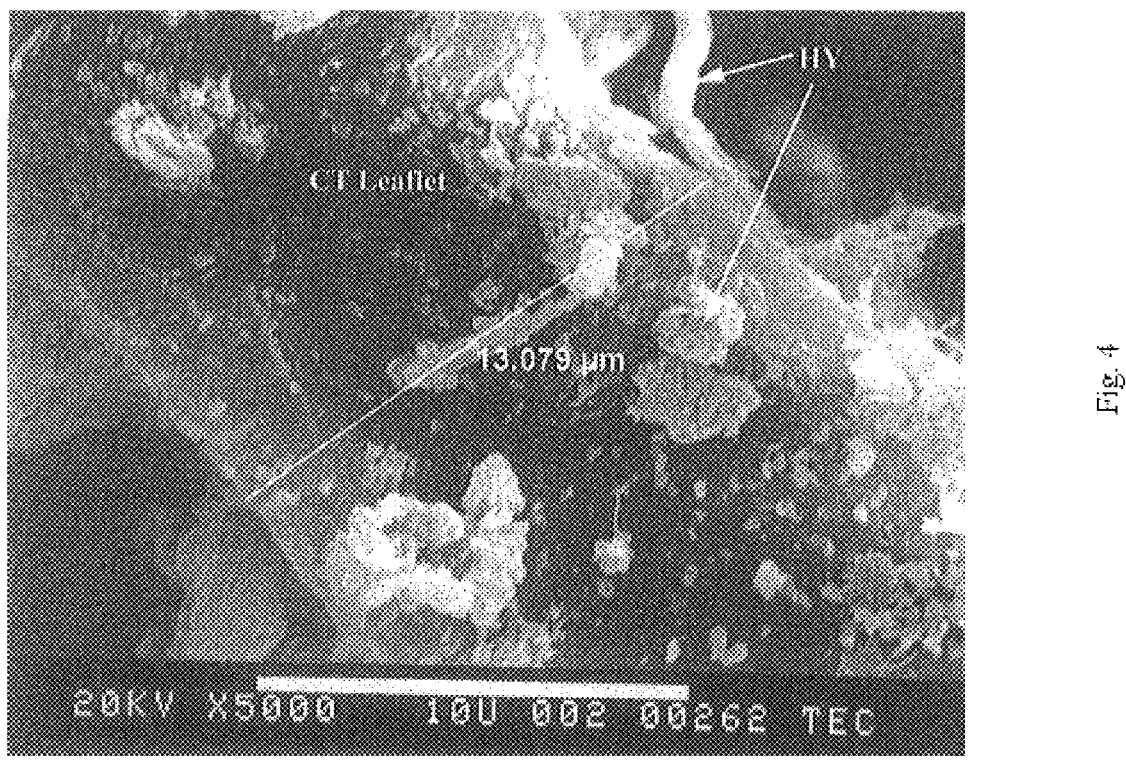
FIG. 4 represents a dry blend mixture of hyaluronic acid and chitosan according to one embodiment of the present invention.
Figure 6:
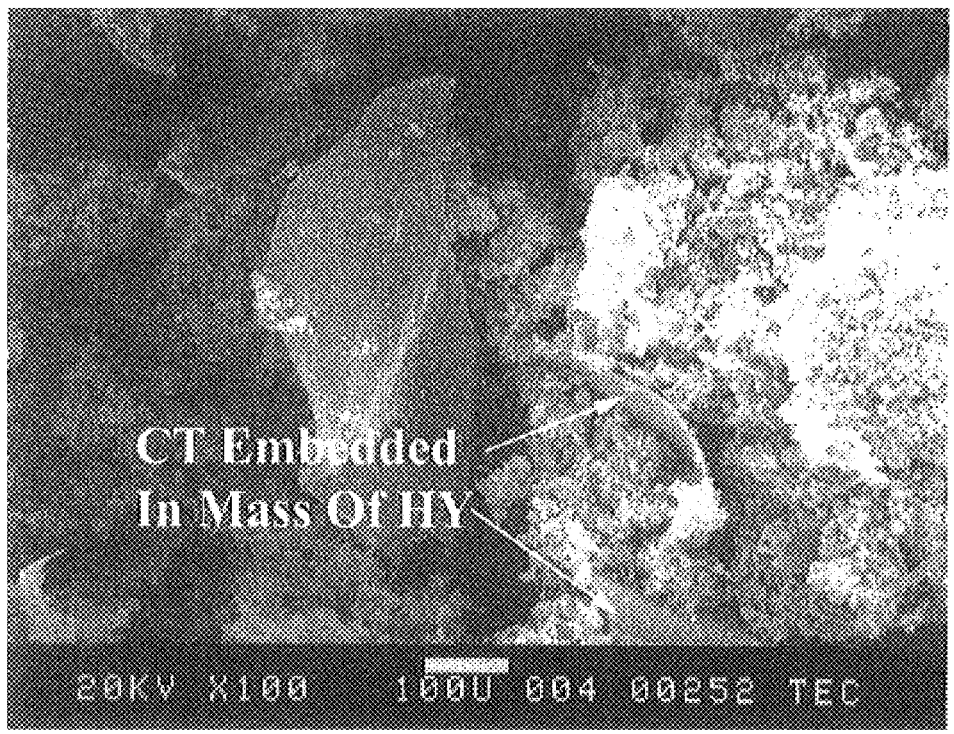

FIGS. 1-4 detail dimensions of typical chitosan leaflets. FIG. 1 is illustrative of a CT leaflet, processed according to one embodiment of the present invention. The flat leaflet yield a good area measurement of 1 mm$^2$. FIGS. 2, 3 and 4 represent the hyaluronan (HY)/chitosan (CT) dry blend mixtures of one embodiment of the present invention. These images show the CT leaflets "on edge" for thickness measurements at magnification. The chitosan leaflet has a thickness of 4.5 μm in FIGS. 2 and 3. FIG. 4 shows a chitosan leaflet with a 13 μm thickness. FIGS. 2-4 also show, at high magnification, the positional relationship of dry CT leaflets and dry HY particles. FIGS. 5 and 6 show, at low magnification, the general relationship of the two reactants in their dry blended forms and provides visual cues to identify each reactant.

When these dry particles are simultaneously exposed to cell transfer solution or culture media (i.e. water based solution), they both dissolve in the water as they come in contact with it. Where CT and HY particles are in intimate contact with each other in the dry state, an insoluble polyelectrolytic complex (PEC) precipitates out of solution forming a network of insoluble PEC fibers throughout the composition.

Where large regions of HY or CT are isolated from each other, there will be collections of pure HY and CT solutions remaining after the PEC reaction is completed. See FIG. 7. The dry blend of CT and HY therefore is hydrated by solution first, the PEC forms in regions where the CT and HY are proximate to one another, and ultimately there remain regions of isolated un-reacted and substantially pure CT and HY in solution. Physical placement of the reactants in their dry state is thus critical to formation of the ultimate HY-CT polyelectrolytic fibers and can be optimized accordingly. The reactant placement is critical with respect to the dry CT leaflet as well. Where a large leaflet of CT is present and physically removed from a significant mass of HY, the CT leaflet will reform in solution post-reaction as a region of CT hydrogel.

FIG. 7 shows the HCP-h composition after the dry HY and CT reactants have been hydrated and the PEC reaction completed. The resulting PEC fiber reinforced hydrogel has also been lyophilized. Regions of unreacted CT and HY are identified. FIG. 7 also shows the insoluble HY-CT-PEC fibers. These leaflets of CT may have small HY particles on their surfaces. At these positions, a HY-CT-PEC fiber will form on the remaining surface of the CT leaflet. FIG. 8 shows a region of unreacted HY after lyophilization. FIG. 9 shows the fiber network on the surface of an unreacted CT leaflet after lyophilization.

FIG. 10 illustrates viable cells after 5 days in a culture comprising the composition of a network of HY-CT-PEC fibers. HT-1080 fibrosarcoma cells have been grown in the culture. The cells have been injected with green florescent protein in enhance visibility.

The HY-CT-PEC fibers remain insoluble and made be thought of as the insoluble particles suspended in a fluid medium, such as the blend of insoluble and soluble components of a colloid. Unreacted HY and CT materials are soluble and together form the viscoelastic and hydrogel components of one composition embodiment of the present invention. The net result of adding water to the dry blend of HY and CT particles is a fiber (PEC) reinforced mixture of viscoelastic gel (HY) and hydrogel (CT).

Thus since the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the appended claims, rather than by the foregoing description, and all changes which come within the meaning and range of equivalency of the claims are intended to be embraced therein.

What is claimed is:

1. A fluid mass composition formed by the process comprising: blending dry hyaluronic acid particles and dry protonated chitosan particles; and adding an aqueous solution to the blend, wherein said fluid mass composition comprises unreacted protonated chitosan hydrogel, unreacted hyaluronic acid viscoelastic gel and polyelectrolytic complex fibers, wherein said polyelectrolytic complex fibers form a three dimensional network throughout the fluid mass composition that surrounds and penetrates the unreacted protonated chitosan hydrogel and the unreacted hyaluronic acid viscoelastic gel and maintains homogeneous regions of the unreacted protonated chitosan hydrogel and the unreacted hyaluronic acid viscoelastic gel.

2. The composition of claim 1, wherein the dry protonated chitosan particles are dry protonated chitosan platelets.

3. The composition of claim 1, wherein the dry protonated chitosan particles are dry protonated chitosan leaflets.

4. The composition of claim 3, wherein the dry protonated chitosan leaflets have a thickness of from about 1 to about 16 micrometers.

5. The composition of claim 3, wherein the dry protonated chitosan leaflets have a dimensional area of about 1 mm.

6. The composition of claim 3, wherein the dry protonated chitosan leaflets are protonated from about 45% to about 100% of available amines.

7. The composition of claim 1, wherein the dry protonated chitosan is formed by a process comprising:
exposing chitosan to an acid to form a solution, wherein the chitosan becomes protonated;
drying the protonated chitosan by lyophilization to form a stiff porous fabric; and
reducing the fabric to discrete, independent particles.

8. The composition of claim 7, wherein the acid is an organic acid.

9. The composition of claim 7, wherein reducing the fabric to discrete particles is accomplished by mechanical agitation.

10. The composition of claim 1 further comprising one or more biologically active agents.

11. The composition of claim 1, wherein the ratio of the dry hyaluronic acid particles to the dry protonated chitosan particles is at about 0.25 to about 0.75 moles to about 0.6 to about 1.0 moles.

12. The composition of claim 1, wherein about 10 μL to about 15 μL of aqueous solution is added to 1 milligram of the dry hyaluronic acid particles and the dry protonated chitosan particles.

13. A malleable three-dimensional cell culture matrix comprised of the composition of claim 1.

14. A tissue engineering material comprised of the composition of claim 1.

15. A biomimetic composition comprising regions of unreacted protonated chitosan hydrogel, regions of unreacted hyaluronic acid viscoelastic gel and polyelectrolytic complex fibers, wherein the polyelectrolytic complex fibers form a three dimensional network which surrounds and penetrates the regions of unreacted protonated chitosan hydrogel and the regions of unreacted hyaluronic acid viscoelastic gel.

16. The composition of claim 10, wherein the biologically active agent is selected from the group consisting of drugs, cytotoxic agents, pharmaceuticals, growth factor proteins, hormones, morphogens, phage vectors, viri vectors, artificial chromosomes, antibiotics, antineoplastics, and anticoagulants.

* * * * *